United States Patent
Tagomori (10) Patent No.: US 10,342,716 B2
(45) Date of Patent: Jul. 9, 2019

(54) ABSORBENT ARTICLE

(71) Applicant: DAIO PAPER CORPORATION, Ehime (JP)

(72) Inventor: Junta Tagomori, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 455 days.

(21) Appl. No.: 15/316,302

(22) PCT Filed: Jun. 11, 2015

(86) PCT No.: PCT/JP2015/066845
§ 371 (c)(1),
(2) Date: Dec. 5, 2016

(87) PCT Pub. No.: WO2015/190548
PCT Pub. Date: Dec. 17, 2015

(65) Prior Publication Data
US 2017/0156944 A1 Jun. 8, 2017

(30) Foreign Application Priority Data
Jun. 13, 2014 (JP) ................. 2014-122039

(51) Int. Cl.
*A61F 13/53* (2006.01)
*A61F 13/475* (2006.01)
(Continued)

(52) U.S. Cl.
CPC ........ *A61F 13/51108* (2013.01); *A61F 13/15* (2013.01); *A61F 13/4704* (2013.01);
(Continued)

(58) Field of Classification Search
CPC .. A61F 13/15; A61F 13/4704; A61F 13/4756; A61F 13/51108; A61F 13/53; A61F 13/533
See application file for complete search history.

(56) References Cited

U.S. PATENT DOCUMENTS 4,781,710 A * 11/1988 Megison ................. A61F 13/47
604/378
5,795,345 A * 8/1998 Mizutani ............. A61F 13/4756
604/380
(Continued)

FOREIGN PATENT DOCUMENTS

JP 2002-531172 9/2002
JP 2008-154820 7/2008
(Continued)

OTHER PUBLICATIONS

International Search Report dated Sep. 1, 2015.

*Primary Examiner* — Susan S Su
(74) *Attorney, Agent, or Firm* — IPUSA, PLLC (57) ABSTRACT

An absorbent article includes a concave groove formed in an absorbent body; and a highly compressed portion formed at a bottom surface of the concave groove, wherein the highly compressed portion includes a first emboss formed by a pattern in which a unit section, obtained by sectioning the concave groove in a longitudinal direction, is repeatedly positively inverted in a longitudinal direction, the first emboss being formed by extending in a width direction while inclining in the longitudinal direction to cross from a side end to the other side end of the concave groove in the unit section, and a second emboss formed along the concave groove at side edge portions, that are opposite of protruding portions of the first emboss that protrude outwardly in the (Continued)

width direction, respectively, and wherein the first emboss and the second emboss are provided to be apart from each other.

4 Claims, 7 Drawing Sheets (51) Int. Cl.
*A61F 13/533* (2006.01)
*A61F 13/511* (2006.01)
*A61F 13/15* (2006.01)
*A61F 13/47* (2006.01)

(52) U.S. Cl.
CPC .......... *A61F 13/4756* (2013.01); *A61F 13/53* (2013.01); *A61F 13/533* (2013.01)

(56) References Cited

U.S. PATENT DOCUMENTS

| | | | | |
|---|---|---|---|---|
| 6,563,013 | B1* | 5/2003 | Murota | A61F 13/4704 604/379 |
| 8,715,258 | B2* | 5/2014 | Munakata | A61F 13/4702 604/380 |
| 2006/0100598 | A1* | 5/2006 | Tamura | A61F 13/4704 604/380 |
| 2006/0276767 | A1* | 12/2006 | Ueminami | A61F 13/4702 604/385.31 |
| 2010/0168707 | A1* | 7/2010 | Nishikawa | A61F 13/4704 604/383 |
| 2011/0060301 | A1* | 3/2011 | Nishikawa | A61F 13/15699 604/358 |
| 2011/0071486 | A1* | 3/2011 | Harada | A61F 13/4704 604/380 |
| 2011/0251575 | A1* | 10/2011 | Kuroda | A61F 13/4704 604/380 |
| 2012/0220971 | A1* | 8/2012 | Harada | A61F 13/4704 604/380 |
| 2012/0271268 | A1* | 10/2012 | Suzuki | A61F 13/15707 604/385.101 |
| 2013/0085464 | A1* | 4/2013 | Kudo | A61F 13/15731 604/380 |
| 2013/0165885 | A1* | 6/2013 | Kurihara | A61F 13/4756 604/380 |
| 2016/0213525 | A1* | 7/2016 | Suzuki | A61F 13/4756 |
| 2016/0250084 | A1 | 9/2016 | Umemoto et al. | |
| 2018/0193204 | A1* | 7/2018 | Tagomori | A61F 13/533 |

FOREIGN PATENT DOCUMENTS

| | | |
|---|---|---|
| JP | 2008-173247 | 7/2008 |
| JP | 2014-027999 | 2/2014 |
| JP | 2015-089382 | 5/2015 |
| WO | 00/32145 | 6/2000 |
| WO | WO-2011136364 A1 * | 11/2011 ....... A61F 13/15731 |

* cited by examiner

ABSORBENT ARTICLE

BACKGROUND OF THE INVENTION

1. Field of the Invention

The present invention mainly relates to an absorbent article used in incontinence pads, sanitary napkins, panty liners, medical pads, toiletries, disposal diapers and the like, and an absorbent article including an absorbent body having a concave groove formed at a front surface thereof along a longitudinal direction thereof.

2. Description of the Related Art

In conventional absorbent articles, an absorbent body is provided between a liquid impermeable backsheet, such as a polyethylene sheet or a non-woven fabric made of laminated polyethylene sheets, and a liquid permeable topsheet, such as a non-woven fabric or a permeable plastic sheet.

This kind of absorbent article has been improved many times, and in particular, various products in which a concave groove is formed at a front surface in a longitudinal direction are provided, as temporarily reserving means and urine diffusing means for receiving a large amount of urine expelling at once by a small area and diffusing it immediately, such as incontinence pads (Patent Document 1 or the like, for example).

The applicant provides, in the previous patent application (following Patent Document 2), an absorbent article in which an absorbent body is provided between a liquid permeable topsheet and a backsheet, a concave groove substantially extending in a longitudinal direction is formed at a surface of the absorbent body at a liquid permeable topsheet side, and a highly compressed portion is formed at a bottom surface of the concave groove. The highly compressed portion is formed by a pattern in which a unit section, obtained by sectioning the concave groove in a longitudinal direction, is repeatedly positively inverted in the longitudinal direction of the groove, the highly compressed portion including an inclined element that is inclined with respect to a width direction of the groove and with respect to the longitudinal direction of the groove to substantially cross from a side end at one side to a side end at the other side of the concave groove in the unit section.

Patent Document 1: Japanese Patent No. 5,105,884
Patent Document 2: Japanese Patent Application No. 2013-229051

As the highly compressed portion with a predetermined pattern is provided at a bottom surface of the concave groove in the absorbent article disclosed in the above described Patent Document 2, effects can be obtained such as deformation of the concave groove when being worn can be prevented because the concave groove is reinforced by the highly compressed portion, and the body fluid can easily diffuse along the longitudinal direction of the groove as being induced by the highly compressed portion.

Figure 10:
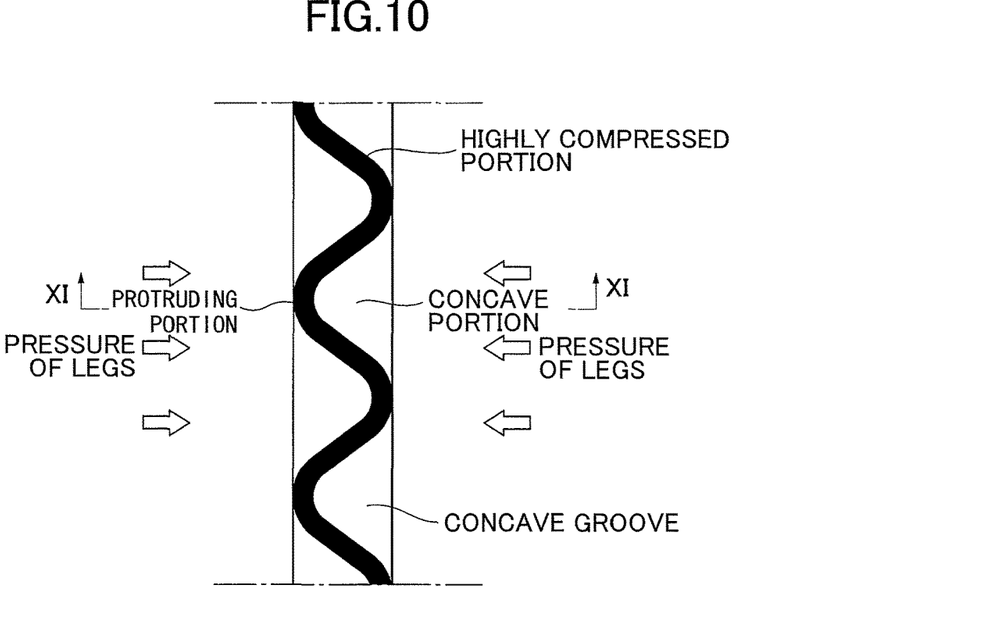
FIG. 10 is an enlarged plan view of a conventional concave groove.
Figure 11:
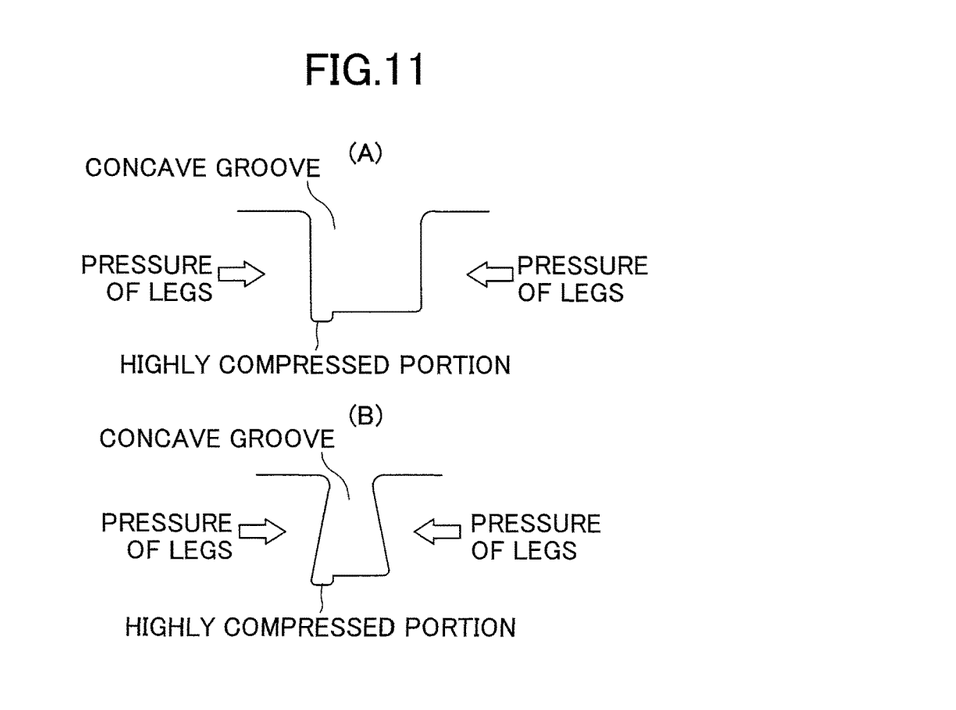

However, as exemplified as an example in the above described Patent Document 2 and illustrated in FIG. 10, if the pattern of the highly compressed portion provided at the bottom surface of the concave groove is formed by a wavy line that extends along the concave groove and repeats a concave portion and a protruding portion at both side in the width direction such that to reciprocate between the both side edges of the concave groove, there are following problems. As illustrated in FIG. 10 and FIG. 11-(A), when a user wears the absorbent article and pressure of legs by root portions of legs is applied from both sides in the width direction, at the protruding portion at which the highly compressed portion protrudes outwardly in the width direction, the protruding portion can function against the pressure of the legs that directs from outside to inside at the side where the protruding portion protrudes and the shape of the concave groove can be retained. However, for the pressure of the legs that directs from outside to inside at the side where the highly compressed portion is concaved, the opposite the above side, as the highly compressed portion that can function against the pressure of legs is not formed, there is a problem that the concave groove is easily collapsed and a space for retaining the body fluid becomes narrow (FIG. 11-(B)).

Further, as the highly compressed portion is provided at the bottom surface of the concave groove, as the liquid permeable topsheet is further drawn for an amount corresponding to the depth of the highly compressed portion, after being drawn for an amount corresponding to the depth of the concave groove, when providing the highly compressed portion, large compression distortion is generated in the front surface material. Thus, there is a risk that splits of the liquid permeable topsheet are generated in compression if a portion at which the direction of the groove drastically changes is provided in a plane pattern of the highly compressed portion. Further, if a fine pattern in which a plurality of closed pattern elements each being surrounded by the highly compressed portion are continuously formed along the concave groove, there are no escapeways for dispersing force applied in compression in the pattern elements. Thus, there are problems such as distortion by the compression is accumulated, splits of the liquid permeable topsheet are generated, an emboss roller is blocked because the liquid permeable topsheet is shaped in a shape of the pattern elements, and runnability is worsened. Further, if the highly compressed portion is formed by a fine pattern, as emboss protruding portions of the emboss roller are also formed by a fine pattern, runnability may be worsened because pulp paper powders are accumulated at cavities between such fine emboss protruding portions.

SUMMARY OF THE INVENTION

The main problem to be solved by the present invention is to provide an absorbent article in which collapse of a concave groove is suppressed, and runnability in embossing is improved.

As the invention of claim 1 to solve the above problem, there is provided an absorbent article including a liquid permeable topsheet; a backsheet; an absorbent body provided between the liquid permeable topsheet and the backsheet; a concave groove, substantially extending along a longitudinal direction, formed at a surface of the absorbent body at a liquid permeable topsheet side; and a highly compressed portion formed at a bottom surface of the concave groove, wherein the highly compressed portion is constituted by a first emboss formed by a pattern in which a unit section, obtained by sectioning the concave groove in a longitudinal direction, is repeatedly positively inverted in a longitudinal direction of the groove, the first emboss being formed by extending in a width direction of the groove while inclining in the longitudinal direction of the groove to cross from a side end at one side to a side end at the other side of the concave groove in the unit section, and a second emboss formed along the concave groove at side edge portions, that are opposite of protruding portions of the first emboss that protrude outwardly in the width direction, respectively, and wherein the first emboss and the second emboss are provided to be apart from each other.

According to the above invention of claim 1, the highly compressed portion constituted by the first emboss and the second emboss are formed at the bottom surface of the concave groove. The first emboss has an wavy-shape in total and is formed by a pattern in which a unit section, obtained by sectioning the concave groove in a longitudinal direction, is repeatedly positively inverted in a longitudinal direction of the groove, and the first emboss is formed by extending in a width direction of the groove while inclining in the longitudinal direction of the groove to cross from a side end at one side to a side end at the other side of the concave groove in the unit section. The wavy-shaped first emboss is provided to reinforce the concave groove at the protruding portions that protrude outwardly in the width direction so that the concave groove is not collapsed, even when pressure of legs is applied that directs from outside to inside at the side at which the protruding portions protrude, by the pressure. On the other hand, only with this wavy-shaped first emboss, there is a problem that, when the pressure is applied that directs from outside to inside at the side (concave portion side) that is opposite of the side at which the protruding portions protrude, as there is no highly compressed portion for reinforcing the concave groove, the concave groove is easily collapsed. Thus, according to the invention, the second emboss is formed along the concave groove at side edge portions, that are opposite of the protruding portions of the wavy-shaped first emboss, respectively. With this, even when the pressure is applied from the direction opposite from the protruding direction of the protruding portion of the wavy-shaped first emboss, as the concave groove is reinforced by the second emboss, collapse of the concave groove is suppressed and the shape of the concave groove can be retained.

Further, according to the invention, the first emboss and the second emboss are provided to be apart from each other. Thus, a portion surrounded by the highly compressed portion is not formed. Thus, the portions between the embosses function as escapeways of the pressure in compression, in embossing, and distortion of the front surface material is dispersed. Thus, distortion of the front surface material due to the compression is not accumulated, and splits of the front surface material can be prevented. Further, as split chips of the front surface material are not generated, blocking of an emboss roller can be eliminated. Furthermore, as emboss patterns are apart from each other, a cavity is not formed at the emboss protruding portion at which paper powders of the absorbent body are filled in the emboss roller. Thus, the emboss roller is hardly blocked and runnability is improved.

As the invention of claim 2, there is provided the absorbent article according to claim 1, wherein the first emboss is formed such that each of the protruding portions, that protrude outwardly in the width direction, is formed by a curved line.

According to the above invention of claim 2, as the protruding portion of the wavy-shaped first emboss, that protrudes outwardly in the width direction, is formed by a curved line, when pressure of legs is applied from outside to inside of the protruding portion, the strength of the protruding portion against the pressure is increased, and the reinforcing effect of the concave groove is furthermore improved.

As the invention of claim 3, there is provided the absorbent article according to claim 1 or 2, wherein the second emboss is formed by a straight line that extends along the concave groove.

According to the above invention of claim 3, by forming the second emboss by the straight line that extends along the concave groove, the second emboss is formed along the side edge of the concave groove. Thus, a broader range can be reinforced against the pressure from outside.

As the invention of claim 4, there is provided the absorbent article according to any one of claims 1 to 3, wherein a distance between the first emboss and the second emboss is greater than or equal to 2 mm and less than or equal to 5 mm.

According to the above invention of claim 4, the distance width between the wavy-shaped first emboss and the second emboss is defined. If the distance width is less than 2 mm, pressure in embossing cannot be dispersed so that wrinkles or the like are easily generated, and blocking of the emboss roller easily occurs. On the other hand, if the distance width is greater than 5 mm, the strength of the concave portion by the wavy-shaped first emboss is not sufficiently reinforced and there is a risk that the concave groove is easily collapsed.

As described above in detail, according to the invention, collapse of a concave groove is suppressed, and runnability in embossing is improved.

BRIEF DESCRIPTION OF THE DRAWINGS

FIG. 6-(A) is a cross-sectional view taken along a VI-VI line of FIG. 5 before being deformed, and FIG. 6-(B) is a cross-sectional view taken along a VI-VI line of FIG. 5 after being deformed;

FIG. 11-(A) is a cross-sectional view taken along a XI-XI of FIG. 10 before being deformed, and FIG. 11-(B) is a cross-sectional view taken along a XI-XI of FIG. 10 after being deformed.

DETAILED DESCRIPTION OF THE PREFERRED EMBODIMENTS

Next, embodiments of the present invention will be described below with reference to drawings.

(Basic Structure of Incontinence Pad 1)

Figure 1:
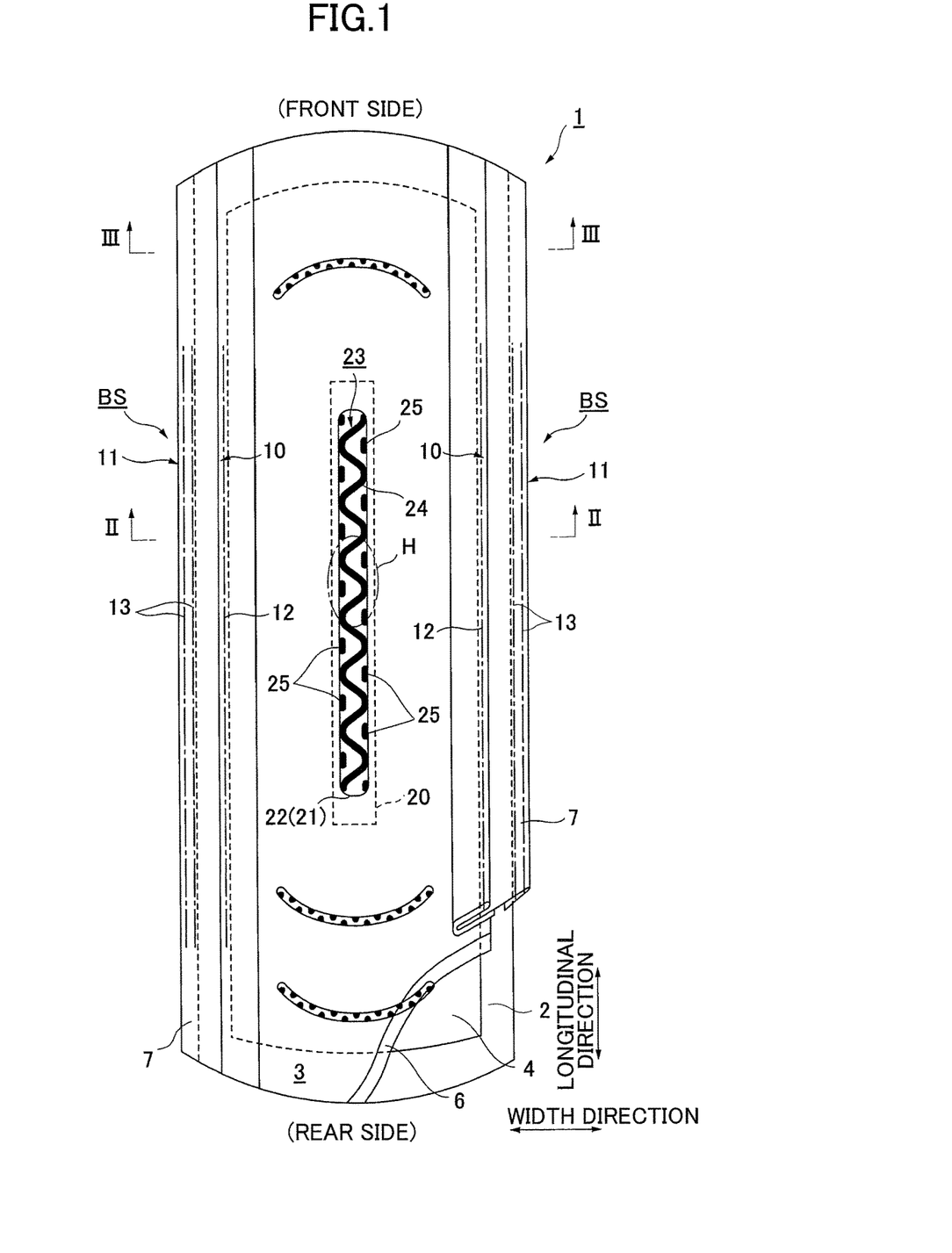
FIG. 1 is a partially broken developed view of an incontinence pad 1 of the invention.
Figure 2:
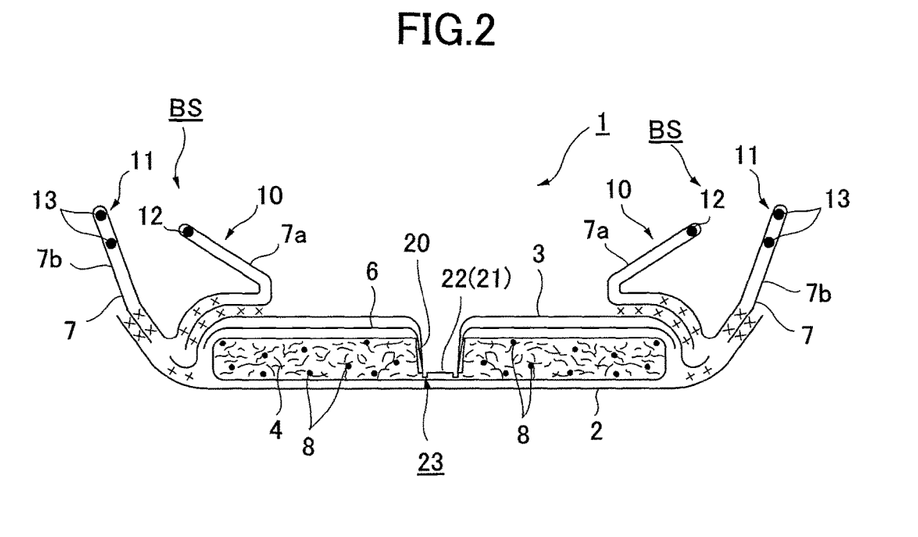
FIG. 2 is a cross-sectional view taken along a II-II line of FIG. 1.
Figure 3:
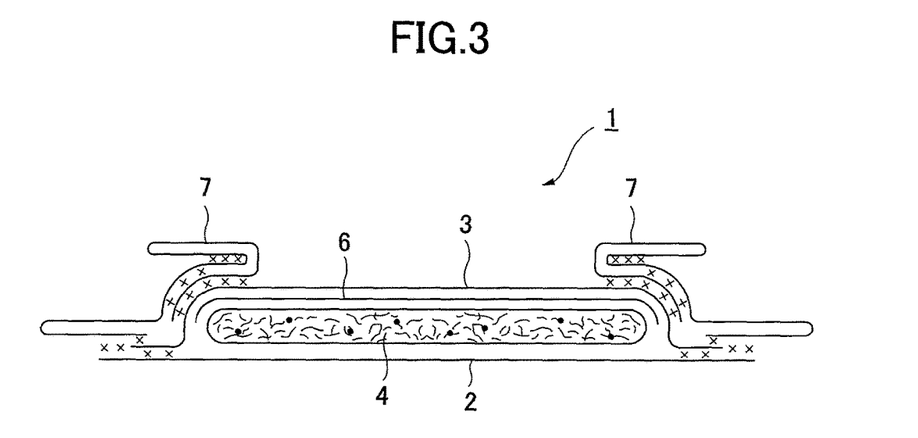
FIG. 3 is a cross-sectional view taken along a III-III line of FIG. 1.

As illustrated in FIG. 1 through FIG. 3, an incontinence pad 1 of the present invention is mainly constituted of a liquid impermeable backsheet 2 made of polyethylene, a liquid permeable topsheet 3 that allows urine and the like to rapidly permeate, an absorbent body 4 made of cotton-like pulp, synthetic pulp, or the like, and that is provided between both the sheets 2 and 3, a hydrophilic second sheet 6 disposed between the liquid permeable topsheet 3 and the absorbent body 4, as necessary, and side non-woven fabrics 7 forming a matched pair of standing gathers BS that protrude toward a skin side in a predetermined zone including at least a body fluid expelling area H in the longitudinal direction, while standing from approximately side edge parts of the absorbent body 4. Around the absorbent body 4, the outer end portions of the liquid impermeable backsheet 2 and the liquid permeable topsheet 3 are bonded with an adhesive such as a hot-melt adhesive or an adhesive means such as a heat seal and the like at end portions in the longitudinal direction, and the liquid impermeable backsheet 2 laterally protruding from the absorbent body 4 and the side non-woven fabrics 7 are bonded with the adhesive such as the hot-melt adhesive or the adhesive means such as the heat seal and the like at the edge portions on both sides. The absorbent body 4 may be surrounded by an encapsulating sheet such as a crepe paper sheet, a non-woven fabric or the like, not illustrated in the drawings, to retain a shape and to improve diffusivity of the absorbent body 4.

Hereinafter, the structure of the incontinence pad 1 is further described in more detail. A sheet material having at least water shielding properties such as polyethylene, polypropylene or the like is used in the liquid impermeable backsheet 2. In addition to this, a non-woven fabric sheet can be also used after ensuring substantial impermeability by providing a waterproof film to cover the non-woven fabric sheet (in this case, the liquid impermeable backsheet is composed of the waterproof film and the non-woven fabric sheet). In recent years, a material having moisture permeability is often preferably used to prevent sweating. A microporous sheet obtained by forming a sheet by melting and kneading inorganic filler in olefin series resin such as polyethylene and polypropylene and then extruding the sheet in one axial direction or two axial directions, is preferably used as the waterproof and moisture permeable sheet material.

Next, a perforated or imperforate non-woven fabric or a porous plastic sheet is preferably used as the liquid permeable topsheet 3. For example, a regenerated fiber such as rayon and cupra, and a natural fiber such as cotton, can be used as a material fiber forming the non-woven fabric in addition to a synthetic fiber including an olefin series such as polyethylene and polypropylene, a polyester series, a polyamide series and the like. As the non-woven fabric, a non-woven fabric obtained by a proper processing method such as a spun lace method, a spun bond method, a thermal bond method, a melt blown method, and a needle punch method, can be used. Among the processing methods, the spun lace method is superior in terms of great flexibility and drape properties, and the thermal bond method is superior in terms of bulkiness and softness.

The absorbent body 4 is, for example, constituted of an absorbable fiber such as a fluff pulp and superabsorbent polymers 8, and is formed into an approximately oval shape extending long in a longitudinal direction of the pad in a planar shape in the illustrated example. The superabsorbent polymers 8 are, for example, formed into granular powders, and are diffused and mixed into the pulp forming the absorbent body 4.

Chemical pulp obtained from wood, a cellulose fiber such as dissolving pulp, and an artificial cellulose fiber such as rayon and acetate, are cited as examples available for the pulp, and softwood pulp having a fiber length longer than that of hardwood pulp is preferably used in terms of function and price. Although not illustrated in the drawings, when the absorbent body 4 is surrounded by the encapsulating sheet, as a result, the encapsulating sheet is provided between the liquid permeable topsheet 3 and the absorbent body 4. Thus, the encapsulating sheet having excellent absorbability serves to rapidly distribute the body fluid and to prevent urine and the like from flowing back. The fabric weight per unit area of the pulp is preferably set in a range of 100 $g/m^2$ to 600 $g/m^2$, and further preferably set in a range of 200 $g/m^2$ to 500 $g/m^2$.

For example, a cross-linking polyacrylate, a self-cross-linking polyacrylate, a saponified substance of a cross-linking copolymer of acrylic acid ester and vinyl acetate, a cross-linking substance of a copolymer of isobutylene and maleic anhydride, a cross-linking polysulfonate, and a partially cross-linking substance of a water swellable polymer such as polyethylene oxide and polyacrylamide are cited as examples of the superabsorbent polymer 8. Among the examples, a substance of acryl acid or an acrylate-based substance having a large amount of water absorption and a high absorption speed is preferable. The water-absorbency (water-absorbing ratio) and the water absorption speed of the superabsorbent polymer having the above-mentioned water absorption performance can be adjusted by adjusting the cross-linking density and the cross-linking density gradient in its manufacturing process. The fabric weight per unit area of the polymer is preferably set in a range of 150 $g/m^2$ to 500 $g/m^2$, and further preferably set in a range of 200 $g/m^2$ to 450 $g/m^2$.

Moreover, a synthetic fiber may be mixed into the absorbent body 4. For example, a polyolefin series such as polyethylene or polypropylene, a polyester series such as polyethylene terephthalate and polybutylene terephthalate, and a polyamide series such as nylon, and a copolymer thereof, or a mixture of two kinds thereof, can be used as the synthetic fiber. Furthermore, a composite fiber such as a core-clad type fiber including a core made of a fiber with a high melting point and a clad made of a fiber with a low melting point, a side-by-side type fiber, and a division type, can be also used. When the synthetic fiber is made of a hydrophobic fiber, it is preferable to treat a surface of the synthetic fiber with a hydrophilic agent so as to have hydrophilic properties to the body fluid.

The second sheet 6 just has to have hydrophilic properties to the body fluid. More specifically, a hydrophilic material that has hydrophilic properties in itself can be used as the second sheet 6 by using the regenerated fiber such as rayon and cupra, and the natural fiber such as cotton. Otherwise, a fiber treated to have the hydrophilic properties by treating a surface of a synthetic fiber including an olefin series such as polyethylene and polypropylene, a polyester series, a polyamide series and the like with a hydrophilic agent, can be used. In addition, the second sheet 6 may include a porous film layer on its back side (the absorbent body 4) to provide tension, may be a stacked layer sheet with the encapsulating sheet, and further may be made of a material including pulp.

On both sides of the front surface side of the present incontinence pad 1, side non-woven fabrics 7 are respectively provided along the longitudinal direction over the entire length of the incontinence pad 1, and outer parts of the side non-woven fabrics 7 extend laterally while the liquid impermeable backsheet 2 extends laterally. Side flaps are formed by attaching the laterally extended side non-woven fabric 7 parts to the laterally extended liquid impermeable backsheet 2 parts with the hot-melt adhesive and the like.

Either water-repellent non-woven fabric or hydrophilic non-woven fabric is used as the side non-woven fabric 7 depending on the desired function. For example, when regarding a function of preventing urine and the like from permeating or of improving a texture as important, it is preferable to use the water-repellent non-woven fabric such as SSMS, SMS or SMMS coated with water-repellent agent and the like of a silicon series, a paraffin series and an alkyl chromic chloride series. When regarding the absorbability of the body fluid as important, it is preferable to use a hydrophilic non-woven fabric obtained by making a swellable or porous synthetic fiber by a method of polymerizing the synthetic fiber in the presence of a compound having a hydrophilic group, for example, an oxidation product of polyethylene glycol, in the manufacture of the synthetic fiber, or a method of treating the surface with a metallic salt such as stannic chloride to partially dissolve the surface to form a porous surface and then to precipitate a metallic hydroxide on the surface, and then providing the hydrophilic property for the synthetic fiber by using capillary action. A fiber obtained by processing the natural fiber, the synthetic fiber or the regenerated fiber by a proper processing method is available for the side non-woven fabric 7.

The side non-woven fabrics 7 are properly folded to form the standing gathers BS of a double structure including the matched pair of inner standing gathers 10, 10 standing from the neighborhood of the edges of the absorbent body 4 toward the skin side, and the matched pair of outer standing gathers 11 that are located outside the inner standing gathers 10, constituted of the liquid impermeable backsheet 2 extending laterally so as to protrude from the absorbent body 4 and the side non-woven fabrics 7, and formed so as to stand toward the skin side. Here, the standing gather BS may have a single gather structure constituted of only one of the inner standing gather 10 or the outer standing gather 11, or may not be formed into a standing gather shape standing toward the skin side by just providing the side non-woven fabric 7 without raising it.

The structure of the inner standing gather 10 and the outer standing gather 11 is described below in more detail. As illustrated in FIG. 2, double sheet parts 7a, 7b are respectively formed on the inner side and the outer side in the width direction by folding both sides of the side non-woven fabric 7 in the width direction. At least one, in the illustrative example, one threadlike elastic stretchable member 12 is fixed at both ends or proper locations in the longitudinal direction, and is provided inside the double sheet part 7a. At least one, in the illustrative example, two threadlike elastic stretchable members 13, 13 are fixed at both ends or proper locations in the longitudinal direction, and are provided inside the double sheet part 7b. By attaching the base edge portion of the double sheet part 7a on the inner side in the width direction to the upper surface of the liquid permeable topsheet 3 provided on a side portion of the absorbent body 4 with a hot-melt adhesive or the like, and attaching the base edge portion of the double sheet part 7b on the outer side in the width direction to the side edge portion of the liquid impermeable backsheet 2 laterally protruding from the absorbent body 4 with the hot-melt adhesive, the inner standing gather 10 standing toward the skin side is formed of the double sheet part 7a on the inner side in the width direction, and the outer standing gather 11 standing toward the skin side is formed of the double sheet part 7b on the outer side in the width direction. Here, as illustrated in FIG. 3, the side non-woven fabric 7 does not include the threadlike elastic stretchable members 12, 13 at the end portions in the longitudinal direction, and the double sheet part 7a on the inner side in the width direction is attached to the absorbent body 4 with a hot-melt adhesive.

(Concave Groove 22)

In the incontinence pad 1, a concave groove 22 that allows body fluids to flow therein is formed at a front surface side (a skin surface side) along the longitudinal direction of the incontinence pad 1. The concave groove 22 receives the body fluid expelled on the surface of the liquid permeable topsheet 3 and temporarily retains the body fluid, while facilitating the diffusion of the body fluid in a front-back direction to increase the absorption speed of the body fluid into the absorbent body 4 and to prevent a side leak of the body fluid.

The concave groove 22 may be formed by integrally compressing constituent members from the liquid permeable topsheet 3 to the absorbent body 4, from the front surface of the liquid permeable topsheet 3. However, it is preferable that the concave groove 22 is formed by previously forming an absorbent body concave portion 20 in the absorbent body 4, and providing an emboss portion 21 that compresses constituent members above the absorbent body 4 by compressing along the absorbent body concave portion 20, from the front surface of the liquid permeable topsheet 3 (skin surface side), because deformation of the concave groove 22 due to the pressure of legs can be prevented.

Figure 4:
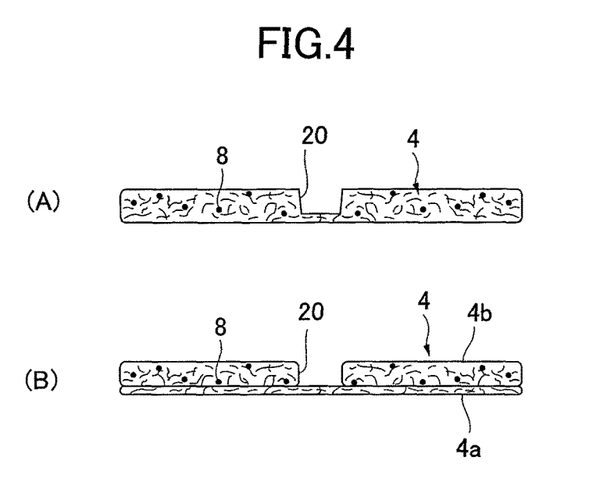
FIG. 4 is a cross-sectional view of an absorbent body 4.

The absorbent body concave portion 20, as a concave groove or a slit, as the concave groove for the illustrated example, is formed in the absorbent body 4 without compression before forming the emboss portion 21. As illustrated in FIG. 4, for example, the absorbent body concave portion 20 is formed by (A) fiber stacking, (B) a staked structure of a lower absorbent body 4a formed by a thickness of a bottom portion of the absorbent body concave portion 20, and an upper absorbent body 4b provided with an opening at a portion corresponding to the absorbent body concave portion 20, or the like, without using compression.

As illustrated in FIG. 1, it is preferable that one absorbent body concave portion 20 is formed at the absorbent body 4 at a center portion in the pad width direction and also at a middle portion in the longitudinal direction corresponding to the body fluid expelling area H. Alternatively, a plurality of absorbent body concave portions 20 may be formed with spaces therebetween in the pad width direction, or the absorbent body concave portions 20 may be formed as a discontinuous line with spaces therebetween in the pad longitudinal direction (not illustrated in the drawings). Here, when the plurality of absorbent body concave portions 20 are formed, it is preferable that the embossed portion 21 is formed for each of the absorbent body concave portions 20.

The plane size of the absorbent body concave portion 20 may have a length of 100 to 180 mm in the longitudinal direction of the pad, and may have a groove width of 5 to 30 mm (a groove width at a bottom surface). When the absorbent body concave portion is formed as the concave groove, it is preferable that the depth of the absorbent body concave portion 20 is greater than or equal to 50% of the thickness of the absorbent body 4, specifically, about 5 to 8 mm.

The fabric weight per unit area of the pulp of the portion of the absorbent body 4 at the bottom portion of the absorbent body concave portion 20 (a portion at the liquid impermeable backsheet 2 side, a portion at a non-skin side) may be 70 $g/m^2$ to 280 $g/m^2$, and preferably, may be 90 $g/m^2$ to 260 $g/m^2$. Further, the fabric weight per unit area of the portion of the absorbent polymer 8 may be 0 $g/m^2$ to 270 $g/m^2$, and preferably, may be 0 $g/m^2$ to 35 $g/m^2$.

When providing the emboss portion 21, its plane size may be larger than the size of the absorbent body concave portion 20, or may be smaller than the size of the absorbent body concave portion 20. The highly compressed portion 23, which is further compressed deeper than a bottom surface of the surrounding concave groove 22, with a predetermined pattern is provided at a bottom surface of the emboss portion 21.

(Highly Compressed Portion 23)

Figure 5:
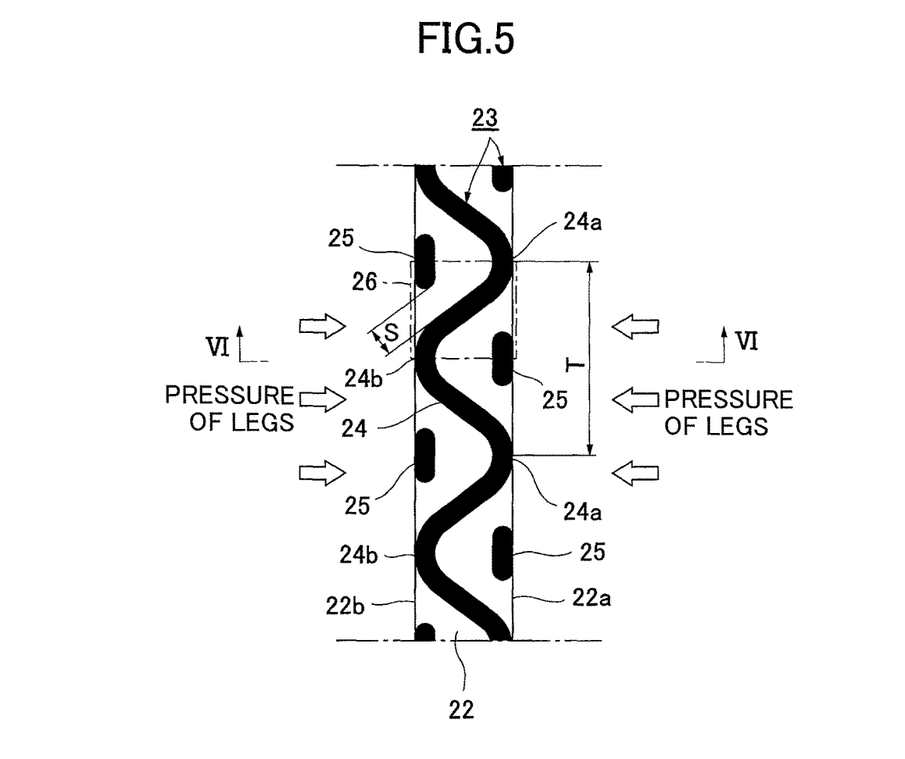
FIG. 5 is an enlarged plan view of a concave groove 22.

Hereinafter, the highly compressed portion 23 is described. The highly compressed portion 23 is a portion that is further compressed to be deeper than a bottom surface of the surrounding concave groove 22, and is formed at the bottom surface of the concave groove 22 with a predetermined pattern. Specifically, as illustrated in FIG. 5, the highly compressed portion 23 is constituted by a wavy-shaped first emboss 24 and a second emboss 25. The wavy-shaped first emboss 24 is formed by a pattern in which a unit section 26, obtained by sectioning the concave groove 22 in a longitudinal direction, is repeatedly positively inverted in a longitudinal direction of the groove, the wavy-shaped first emboss 24 being formed by extending in the width direction of the groove while inclining in the longitudinal direction of the groove to cross from a side end at one side to a side end at the other side of the concave groove 22 in the unit section, in a planar view. The wavy-shaped first emboss 24 is formed by a pattern that extends along the concave groove 22 in total, and that concaves and protrudes repeatedly at both sides in the width direction such that to reciprocate between the both side edges of the concave groove 22. The second emboss 25 is formed along the concave groove 22 at a side edge portion of the concave groove 22, that is opposite of each of protruding portions 24a and 24b of the wavy-shaped first emboss 24 that protrude outwardly in the width direction, respectively.

The wavy-shaped first emboss 24 is a continuous line formed in a wave shape such as a wavy-shaped curved line, a zig-zag line (see FIG. 8) or the like that reciprocates between one side edge 22a and the other side edge 22b of the concave groove 22. In the wavy-shaped first emboss 24, the protruding portion 24a that protrudes toward the one side edge 22a and the protruding portion 24b that protrudes toward the other side edge 22b are alternatively repeatedly provided. Further, the wavy-shaped first emboss 24 is formed such that a single emboss line extends in the same direction of the longitudinal direction of the groove, without crossing or being connected. Thus, a closed area surrounded by an emboss line is not provided at the bottom surface of the concave groove 22.

It is preferable that the wavy-shaped first emboss 24 is formed at the entire width of the concave groove 22. This means that the first emboss 24 is provided such that apex portions of the protruding portions 24a and 24b match or are in the vicinity of the side edges 22a and 22b of the concave groove 22, respectively. With this, the entire width of the concave groove 22 can be reinforced, and collapse of the concave groove 22 due to pressure from both sides in the width direction can be surely prevented. The above described "in the vicinity" means that the apex portions of the protruding portions 24a and 24b are provided inside the side edges 22a and 22b of the concave groove 22, respectively, within a range that is less than or equal to 2 mm, preferably, less than or equal to 1 mm.

As illustrated in FIG. 5, it is preferable that the wavy-shaped first emboss 24 is formed by a curved line that bulges outward in the width direction with radius. With this, the collapse due to the pressure from outsides can be surely prevented. It is preferable that the wavy-shaped first emboss 24 is formed in a sine wave shape, in total, however, may be formed by a pattern in which a semicircular ark is alternately reversely repeatedly provided.

The distance T (a period of the wavy-shaped first emboss 24) between two adjacent protruding portions 24a of the wavy-shaped first emboss 24 at the same side may be 16 mm to 25 mm, preferably, may be 18 mm to 22 mm. With this, the concave groove 22 can be surely reinforced, wrinkles, twists and splits of the front surface material can be prevented and runnability is improved. The wavy-shaped first emboss 24 is formed to have substantially the same distance T for the entire length of the concave groove 22 (formed at substantially the same period).

Meanwhile, the second emboss 25 is a plurality of embosses each of which is formed as a continuous line along the longitudinal direction of the concave groove 22 at a predetermined range. The second emboss 25 is formed along the concave groove 22 means that a straight line connecting end portions of each of the embosses substantially extends along the longitudinal direction of the concave groove 22, and includes, in addition to a case in which the straight line is parallel to the longitudinal direction of the groove line, a case in which the straight line has an angle difference with respect to the longitudinal direction of the groove line within about ±20°. Further, the line extending along the longitudinal direction is not necessarily a straight line, and may be formed by a curved line, a polygonal line, a wavy line or the like.

The second emboss 25 is formed at side edge portions of the concave groove 22, that are opposite of protruding portions 24a and 24b of the wavy-shaped first emboss 24 that protrude outwardly in the width direction, respectively. This means that at the protruding portion 24a that protrudes toward the one side edge 22a of the concave groove 22, the second emboss 25 is formed along the opposing other side edge 22b, and at the protruding portion 24b that protrudes toward the other side edge 22b of the concave groove 22, the second emboss 25 is formed along the opposing one side edge 22a.

The second emboss 25 is provided such that an edge portion at the outer side matches the side edge 22a or 22b of the concave groove 22, or in the vicinity of the side edge 22a or 22b of the concave groove 22. In the vicinity means that the edge portion of the second emboss 25 at the outer side is provided at inside the side edges 22a and 22b of the concave groove 22 within a range that is less than or equal to 2 mm, preferably, less than or equal to 1 mm. With this, similar to the wavy-shaped first emboss 24, the concave groove 22 can be reinforced for a large range in the width direction.

By providing the wavy-shaped first emboss 24 to reciprocate between the both side edges 22a and 22b of the concave groove 22, and providing the second emboss 25 at side edge portions 22a and 22b of the concave groove 22, the first emboss 24 and the second emboss 25 are provided to overlap in the longitudinal direction of the groove. With this, the wavy-shaped first emboss 24 and the second emboss 25 are provided to have resistance forces against pressure of legs from outside in the width direction at the same position in the width direction of the groove It is preferable that the second emboss 25 is formed by a straight line extending along the longitudinal direction of the concave groove 22 within a predetermined range at which the wavy-shaped first emboss 24 becomes a concave portion. With this, as the second emboss 25 is provided along the side edge of the concave groove 22, a broader range of reinforcement can be obtained against the pressure from outside at the side where the second emboss 25 is provided.

The second emboss 25 is provided at a position in the width direction of the groove such that its center portion in the longitudinal direction of the groove matches an apex portion of each of the protruding portions 24a and 24b of the wavy-shaped first emboss 24. This means that if a groove width direction line is drawn at the apex portion of each of the protruding portions 24a and 24b of the wavy-shaped first emboss 24, the second emboss 25 is formed to have the same lengths in the longitudinal direction of the groove at both sides of the groove width direction line as a center.

Further, the wavy-shaped first emboss 24 and the second emboss 25 are formed not to be connected with each other and to be apart from each other such that the emboss lines are independent from each other in the incontinence pad 1. Thus, the highly compressed portion 23 is formed by a single continuous first emboss 24 that extend along the concave groove 22, and the second emboss 25 is provided at each of the concave portions of the wavy-shaped first emboss 24. This means that a plurality of the second embosses 25 are provided at predetermined positions, apart from each other, in the concave groove 22.

As illustrated in FIG. 5, it is preferable that the distance width S between the wavy-shaped first emboss 24 and the second emboss 25, at which a straight line between both embosses becomes the shortest, is greater than or equal to 2 mm and less than or equal to 5 mm (2 mm≤S≤5 mm). If this distance width S is less than 2 mm, the pressure in emboss compression is difficult to be dispersed, and wrinkles and the like are easily generated and an emboss roller is easily blocked because paper powders enter space portions. On the other hand, if the distance width S is greater than 5 mm, the concave portion of the wavy-shaped first emboss 24 are not sufficiently reinforced and the concave groove 22 is easily collapsed.

Figure 6:
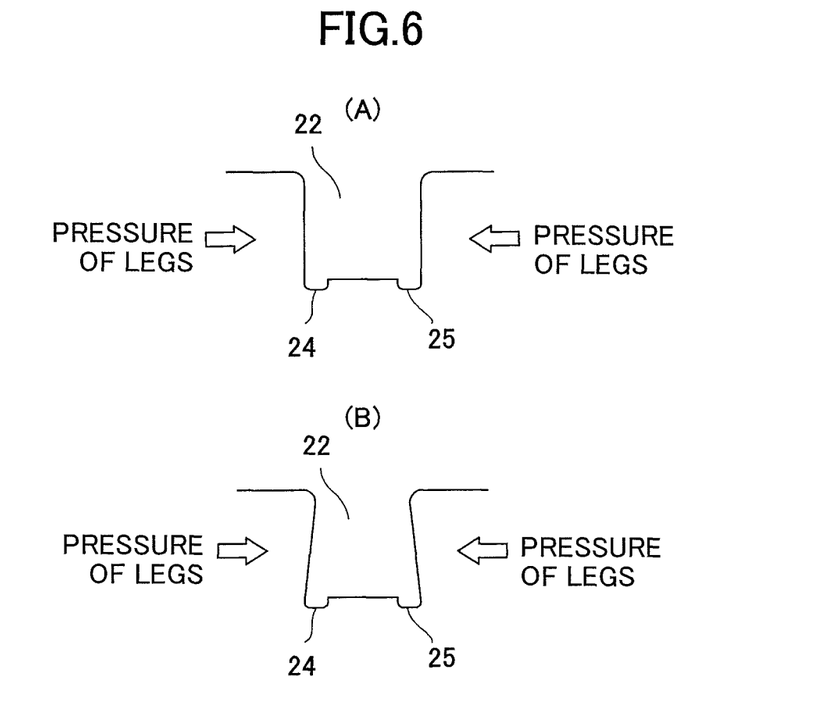
Figure 9:
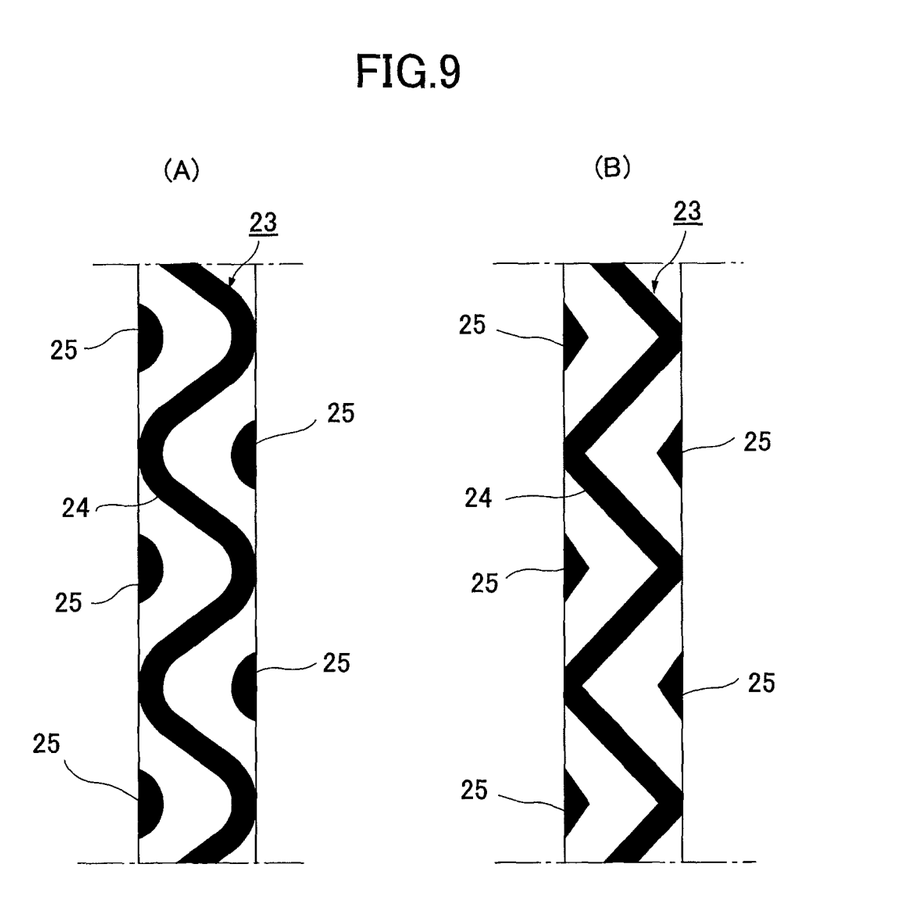
FIG. 9 is an enlarged plan view of the concave groove 22 of another embodiment.

As described above in detail, the highly compressed portion 23 constituted by the wavy-shaped first emboss 24 and the second emboss 25 is formed at the bottom surface of the concave groove 22 in the incontinence pad 1. If the highly compressed portion is constituted by only the wavy-shaped first emboss 24, as illustrated in FIG. 9 and FIG. 10, resistance force against pressure of legs from outside in the width direction becomes weak at a concave portion at which the wavy-shaped emboss is not formed. Thus, the concave groove collapses to reduce the reserving volume of the body fluid of the concave groove and the body fluid is difficult to be absorbed in the absorbent body. On the other hand, according to the incontinence pad 1, as illustrated in FIG. 6, the second emboss 25 is provided at a portion corresponding to the concave portion of the wavy-shaped first emboss 24. Thus, resistance force become large against pressure of legs from both side in the width direction, and the concave groove 22 is hardly collapsed.

Further, the wavy-shaped first emboss 24 and the second emboss 25 are not connected with each other in the incontinence pad 1, and each of the emboss lines are independently formed to be apart from each other. Thus, no area is formed at the bottom surface of the concave groove 22 that is surrounded by the continuous highly compressed portion 23. Therefore, portions between the embosses function as escapeways for compression force when embossing to disperse the pressure. Thus, distortion of the front surface material by the compression is not accumulated, splits of the front surface material, blocking of the emboss roller and the like are not generated, and runnability is improved.

Here, it is preferable that the fabric weight per unit area of the superabsorbent polymer 8 provided at the bottom portion of the absorbent body concave portion 20 of the absorbent body 4 is smaller than that at other areas in the incontinence pad 1 in order to prevent splits of the front surface material when forming the highly compressed portion 23. If a large amount of the superabsorbent polymer 8 is provided at this area, splits are easily generated in the front surface material due to the superabsorbent polymer 8. Thus, by reducing the amount of polymer, risk of generation of splits in embossing is reduced.

Figure 7:
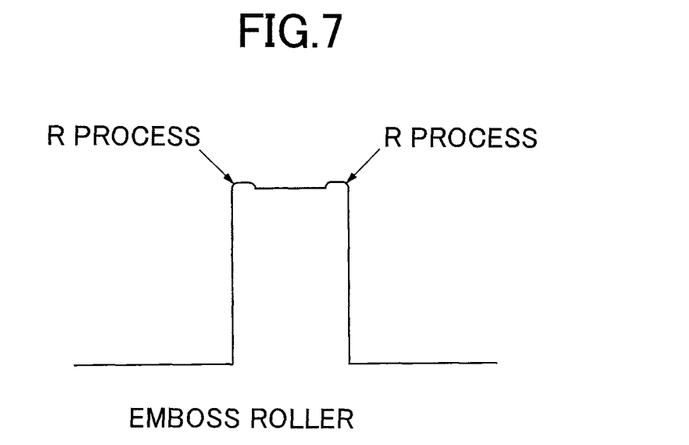
FIG. 7 is a cross-sectional view illustrating an emboss protruding portion of an emboss roller.

Further, when providing the highly compressed portion 23, the emboss roller provided with an emboss protruding portion of a predetermined pattern is used. As illustrated in FIG. 7, it is preferable that an R process (R chamfering) is performed at corner portions at a front end of the emboss protruding portion of the emboss roller. With this, compared with corner portions at which the R process is not performed, or corner portions at which a C process of chamfering is performed, splits of the liquid permeable topsheet 3 can be surely prevented.

Further, groove widths and depths of the wavy-shaped first emboss 24 and the second emboss 25 may be different, however, it is preferable that they are the same so that uniform resistance forces are generated against pressures from both sides in the width direction.

Other Embodiments (1) In the above embodiment, the highly compressed portion 23 is integrally provided to the constituent members from the liquid permeable topsheet 3 to the absorbent body 4 by the compression from the front surface of the liquid permeable topsheet 3. However, the highly compressed portion 23 may be provided only to the absorbent body 4 by compression from a front surface of the absorbent body 4, or may be integrally provided to the encapsulating sheet and the absorbent body 4 by compression from a front surface of the encapsulating sheet. By providing the highly compressed portion 23 at least in the absorbent body 4, deformation of the concave groove when being worn can be prevented, and the body fluid easily diffuses in the longitudinal direction of the groove.

Figure 8:
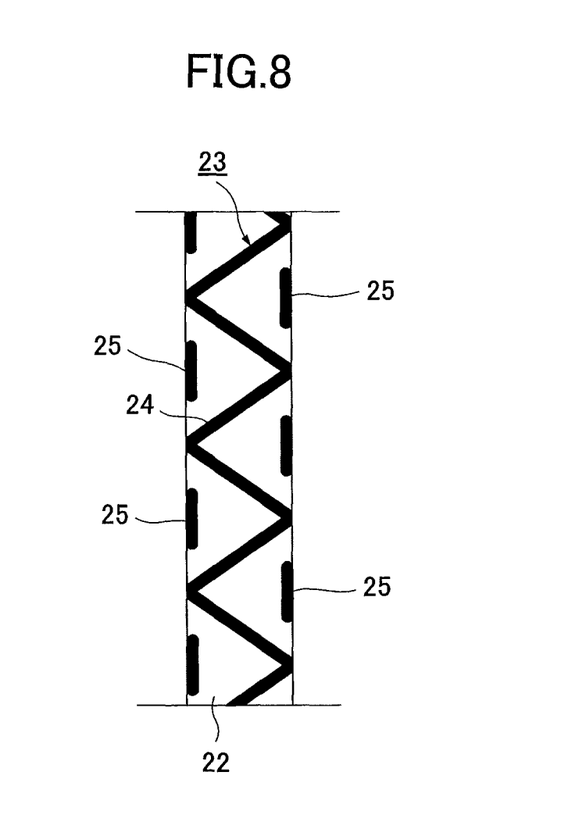
FIG. 8 is an enlarged plan view of the concave groove 22 of another embodiment.

(2) As long as the wavy-shaped first emboss 24 is formed by a pattern in which the unit section 26, obtained by sectioning the concave groove 22 in the longitudinal direction, is repeatedly positively inverted in the longitudinal direction of the groove, the wavy-shaped first emboss 24 being formed by extending in the width direction of the groove while inclining in the longitudinal direction of the groove to cross from a side end at one side to a side end at the other side of the concave groove 22 in the unit section 26, as illustrated in FIG. 8, each of the protruding portions 24a and 24b that protrude outwardly in the width direction may be formed in a triangle shape, a trapezoidal shape, or a square shape.

(3) As long as the second emboss 25 is formed along the concave groove 22, as illustrated in FIG. 9, the second emboss 25 may be formed by a plane pattern whose plane shape is (A) a semicircle shape, (B) a triangle shape or the like. Further, as illustrated in FIG. 9-(A), when the wavy-shaped first emboss 24 is formed by a curved line, it is preferable that the second emboss 25 is formed to have a semicircle shape whose outline of the emboss is a curved line corresponding to the curved line of the wavy-shaped first emboss 24. As illustrated in FIG. 9-(B), when the wavy-shaped first emboss 24 is formed by a zig-zag line, which is a straight line, it is preferable that the second emboss 25 is formed to have a triangle patter whose outline of the emboss is a straight line corresponding to the zig-zag line of the wavy-shaped first emboss 24.

NUMERALS

1 . . . incontinence pad, 2 . . . liquid impermeable backsheet, 3 . . . liquid permeable topsheet, 4 . . . absorbent body, 6 . . . second sheet, 7 . . . side non-woven fabric, 8 . . . superabsorbent polymer, 10 . . . inner standing gather, 11 ... outer standing gather, 12, 13 ... threadlike elastic stretchable member, 20 ... absorbent body concave portion, 21 ... emboss portion, 22 ... concave groove, 23 ... highly compressed portion, 24 ... first emboss, 25 ... second emboss

What is claimed is:

1. An absorbent article comprising:
   a liquid permeable topsheet;
   a backsheet;
   an absorbent body provided between the liquid permeable topsheet and the backsheet;
   a concave groove, substantially extending along a longitudinal direction, formed at a surface of the absorbent body at a liquid permeable topsheet side; and
   a highly compressed portion formed at a bottom surface of the concave groove,
   wherein the highly compressed portion includes
      a first emboss formed by a pattern in which a unit section, obtained by sectioning the concave groove in a longitudinal direction, is repeatedly positively inverted in a longitudinal direction of the groove, the first emboss being formed by extending in a width direction of the groove while inclining in the longitudinal direction of the groove to cross from a side end at one side to a side end at the other side of the concave groove in the unit section, and
      a second emboss formed along the concave groove at side edge portions, that are opposite of protruding portions of the first emboss that protrude outwardly in the width direction, respectively, and
   wherein the first emboss and the second emboss are provided to be apart from each other.

2. The absorbent article according to claim 1, wherein the first emboss is formed such that each of the protruding portions, that protrude outwardly in the width direction, is formed by a curved line.

3. The absorbent article according to claim 1, wherein the second emboss is formed by a straight line that extends along the concave groove.

4. The absorbent article according to claim 1, wherein a distance between the first emboss and the second emboss is greater than or equal to 2 mm and less than or equal to 5 mm.

* * * * *